US008173783B2

(12) United States Patent
Chiou

(10) Patent No.: US 8,173,783 B2
(45) Date of Patent: *May 8, 2012

(54) PROCESS FOR SELECTIVELY ISOLATING IGY ANTIBODIES FROM EGG YOLK OF AN ANSERIFORM BIRD AND IGY ANTIBODIES OBTAINED THEREBY

(75) Inventor: Victor Chiou, Taichung (TW)

(73) Assignee: Good Biotech Corporation, Taichung (TW)

(*) Notice: Subject to any disclaimer, the term of this patent is extended or adjusted under 35 U.S.C. 154(b) by 731 days.

This patent is subject to a terminal disclaimer.

(21) Appl. No.: 11/409,515

(22) Filed: Apr. 21, 2006

(65) Prior Publication Data
US 2006/0223986 A1 Oct. 5, 2006

Related U.S. Application Data

(63) Continuation-in-part of application No. 10/209,006, filed on Jul. 31, 2002, now abandoned, which is a continuation-in-part of application No. 09/733,210, filed on Dec. 8, 2000, now Pat. No. 6,680,376.

(51) Int. Cl.
G01N 33/08 (2006.01)
C07K 17/02 (2006.01)

(52) U.S. Cl. ............ 530/413; 530/389.1; 530/415; 530/416

(58) Field of Classification Search .......... None
See application file for complete search history.

(56) References Cited

U.S. PATENT DOCUMENTS

| 4,511,473 | A | 4/1985 | Hou |
| 4,550,019 | A | 10/1985 | Polson |
| 5,340,923 | A | 8/1994 | Carroll |
| 5,367,054 | A | 11/1994 | Lee |
| 5,585,098 | A | 12/1996 | Coleman |
| 5,601,823 | A | 2/1997 | Williams et al. |
| 5,728,813 | A | 3/1998 | Lyman et al. |
| 5,922,359 | A | 7/1999 | Youssefyeh |
| 5,976,519 | A | 11/1999 | Nojiri et al. |
| 6,608,172 | B1 * | 8/2003 | Chiou ............ 530/413 |
| 6,680,376 | B2 * | 1/2004 | Chiou ............ 530/413 |

FOREIGN PATENT DOCUMENTS

| DE | 100 29 705 A1 | 1/2002 |
| DE | 100 65 227 A1 | 7/2002 |
| EP | 0 503 293 A1 | 9/1992 |
| JP | 64-38098 | 2/1989 |
| JP | 06-128298 | 5/1994 |
| JP | 06-192127 | 7/1994 |
| JP | 08-127600 | 5/1996 |
| JP | 9-239203 | 9/1997 |
| JP | 2002-030100 | 1/2002 |

OTHER PUBLICATIONS

Akita et al., "Comparison of four purification methods for the production of immunoglobulins from eggs laid by hens immunized with an enterotoxigenic E. coli strain", Journal of Immunological Methods 160:207-214 (1993).

Akita et al., "Immunoglobulins from Egg Yolk: Isolation and Purification", Journal of Food Science 57:629-634 (1992).

Akita et al., "Production and purification of Fab' fragments from chicken egg yolk immunoglobulin Y (IgY)", Journal of Immunological Methods 162:155-164 (1993).

Brüssow et al., "Bovine Milk Immunoglobulins for Passive Immunity to Infantile Rotavirus Gastroenteritis", Journal of Clinical Microbiology 25:982-986 (1987).

Gottstein et al., "Egg yolk immunoglobulin Y as an alternative antibody in the serology of echinococcosis", Z. Parasitenkd 71:273-276 (1985).

Grey, "Duck Immunoglobulins: I. Structural Studies on a 5.7S and 7.8S γ-Globulin", Journal of Immunology 98:811-819 (1967).

Harlow et al. in Antibodies: A Laboratory Manual, 1998, Cold Spring Harbor Haboratory Publication, Cold Spring Harbor, NY, pp. 298-299, 292-293, and 658.

U.S. Appl. No. 09/591,665, Jun. 9, 2000, Chiou.

Hassl et al., "Purification of egg yolk immunoglobulins: A two-step procedure using hydrophobic interaction chromatography and gel filtration", Journal of Immunological Methods 110:225-228 (1988).

Hatta et al., "Separation of Phospholipids from Egg Yolk and Recovery of Water-Soluble Proteins", Journal of Food Science 53:425-431 (1988).

Higgins et al., "Purification of duck immunoglobulins: an evaluation of protein A and protein G affinity chromatography", Vet Immunol. Immunopathol. 44:169-180 (1995).

Jens Chr Jensenius et al., "Eggs: Conveniently Packaged Antibodies. Methods for Purification of Yolk IgG", Journal of Immunological Methods 46:63-68 (1981).

Lamoyi, "Preparation of F(ab')$_2$ Fragments from Mouse IgG of Various Subclasses", Methods in Enzymology 121:652-663 (1986).

Litman et al., "Active Sites of Turtle and Duck Low Molecular Weight Antibody to 2'4' Dinitrophenol", Immunochemistry 10:323-329 (1973).

Losonczy et al., "ELISA for the measurement of IgY concentrations of hen's and quail's serum and yolk", INABIS 2000, $6^{th}$ Internet World Congress for Biomedical Sciences, Poster #47.

Magor et al., "Structural Relationship Between the Two IgY of the Duck, Anas latyrhynchos: Molecular Genetic Evidence", Journal of Immunology 149:2627-2633 (1992).

Muratsugu et al., "Adsorption and Desorption of F(ab')$_2$ Anti-hIgG on Plasma-Polymerized Allylamine Thin Film: The Application of the Film to Immunoassay", Journal of Colloid and Interface Science 147:378-386 (1991).

Narhi et al., "Effect of Three Elution Buffers on the Recovery and Structure of Monoclonal Antibodies", Analytical Biochemistry 253:236-245 (1997).

Ortega-Vinuesa et al., "Particle enhanced immunoaggregation of F(ab')$_2$ molecules", Journal of Immunological Methods 190:29-38 (1996).

(Continued)

Primary Examiner — Yunsoo Kim
(74) Attorney, Agent, or Firm — Fish & Richardson P.C.

(57) ABSTRACT

The present invention mainly relates to a process for isolation and purification of yolk antibodies from egg yolk of an anseriform bird by an adsorption chromatographic procedure using a water insoluble non-charged absorbent to accomplish a desired separation of yolk antibodies, and by a salting-out procedure that differentially precipitates the IgY antibodies. The present invention also relates to the yolk antibodies produced thereby and various uses of such yolk antibodies.

21 Claims, 8 Drawing Sheets

OTHER PUBLICATIONS

Otani et al., "Comparative Studies on Properties of Hen Egg Yolk IgY and Rabbit Serum IgG Antibodies", *Lebsensm.-Wiss. U-Technol.* 24:152-158 (1991).

Polson et al., "Isolation of Viral IgY Antibodies from Yolks of Immunized Hens", *Immunological Communications* 9:475-493 (1980).

Tacket et al., "Protection by Milk Immunoglobulin Concentrate Against Oral Challenge with Enterotoxigenic *Escherichia coli*", *The New England Journal of Medicine* 318:1240-1243 (1988).

Toth et al., "Humoral Immune Response of the Duck to Duck Hepatitis Virus: Virus-Neutralizing vs. Virus-Precipitating Antibodies", *Avian Diseases* 25:17-28 (1980).

Unanue et al., "V. Studies on the Interaction of Nephrotoxic Antibodies with Tissues of the Rat", *Experimental Glomerulonephritis* 697-714 (1965).

Zimmerman et al., "Structural Studies on the Duck 5.7S and 7.8S Immunoglobulins", *Biochemistry* 10:482-488 (1971).

Hansen et al., "Isolation and purification of immunoglobulins from chicken eggs using thiophilic interaction chromatography", *J. Immunol. Methods* 215:1-7 (1998).

Fichtali, J. et al., "Purification of Antibodies from Industrially Separated Egg Yolk", *Journal of Food Science*, vol. 58, No. 6 pp. 1282-1290; 1993.

Svendsen, L. et al., "Development and Comparision of Purification Strategies for Chicken Antibodies from Egg Yolk", *Laboratory Animal Scienc*, vol. 45, No. 1, pp. 89-93; 1995.

Behn et al., "Use of Polyclonal Avian Antibodies", *Springer Lab Manuals. Chicken Egg Yolk Antibodies, Production and*, 108-210 (2001).

Staak et al., "Isolation of IgY from Yolk", *Springer Lab Manuals. Chicken Egg Yolk Antibodies, Production and*, 65-107 (2001).

Warr et al., "IgY: clues to the origins of modern antibodies", *Immunology Today* 16(8):392-398 (1995).

Hatta et al., "A Novel Isolation Method for Hen Egg Yolk Antibody, 'IgY'", *Agric. Biol. Chem.*, 54(10):2531-2535 (1990).

* cited by examiner

PROCESS FOR SELECTIVELY ISOLATING IGY ANTIBODIES FROM EGG YOLK OF AN ANSERIFORM BIRD AND IGY ANTIBODIES OBTAINED THEREBY

RELATED APPLICATIONS

This application is a continuation-in-part of and claims priority to U.S. application Ser. No. 10/209,006, filed Jul. 31, 2002 now abandoned, which is a continuation-in-part of and claims priority to U.S. application Ser. No. 09/733,210, filed Dec. 8, 2000 now U.S. Pat. No. 6,680,376, the contents of which are incorporated herein by reference in their entirety.

BACKGROUND OF THE INVENTION

1. Field of the Invention

The present invention relates to a process for rapid isolation and purification of yolk antibodies, in particular IgY antibody, from anseriform bird yolk, and the yolk antibodies obtained thereby. More particularly, the present invention relates to a process for isolation and purification of yolk antibodies from anseriform bird yolk by an adsorption chromatographic procedure using a porous water insoluble non-charged adsorbent to accomplish a desired separation of yolk antibodies, and by a salting-out procedure that differentially precipitates the IgY antibodies. The present invention also relates to uses of the IgY antibodies in quantitative or qualitative immunoassay or in the preparation of pharmaceutical compositions directing to an etiological agent of interest.

2. Description of the Related Art

Antibodies are used widely in many biological investigations and clinical applications. Sera obtained from hyperimmunized mammalians are the most common source of polyclonal antibodies. Antibodies derived from such immune sera belong to a group of proteins called "immunoglobulins," among which the immunoglobulin G (IgG) is the most abundant. The IgG molecule consists of three domains, namely two Fab regions and one Fc region. The Fab portion involves mainly in antigen binding. The Fc portion, though having no ability to bind with an antigen, directs several biological activity of an antibody, such as complement fixing and Fc receptor binding.

In the art of immunodiagnostics, an intact IgG molecule is not suitable for use in detection systems and immunological assays involving mammalian sera since the Fc region on an IgG molecule is capable of binding to Fc receptors, activating the complement system, and reacting with rheumatoid factor in mammalian sera. Removal of the Fc portion of an IgG molecule frequently leads to a reduction in the interference (E. Lamoyi, *Methods in Enzymology* 121:652-663, 1986).

Some of the suggested uses of antibody in immunotherapy include treating patients with intoxicated bacterial toxins or snake venoms (see, for example, U.S. Pat. No. 5,340,923 and U.S. Pat. No. 5,601,823), and protection of neonatal piglets against fatal enteric colibacillosis (see, for example, H. Brussow et al., *J. Clin. Microbiol.* 25:982, 1987; and C. O. Tacket et al., *New Eng. J. Med.* 318:1240, 1988). Since the Fc fragment of an antibody molecule is known to be the most antigenic portion of the immunoglobulin (E. M. Akita et al., *J. Immunol Methods.* 162:155-164, 1993), cleavage of the same which results in the formation of an F(ab')$_2$ fragment will reduce significantly a number of potential allergenic sites on the immunoglobulin molecule and is thus beneficial to human or animals administered with the immunoglobulin.

Recently, the divalent F(ab')$_2$ antibody fragment has been shown to be more useful in the immunodiagnostic tests (M. Muratsugu et al., *J. Colloid Interface Sci* 147:378, 1991; and J. L. Ortega-Vinuesa et al., *J. Immunol Methods* 90:29, 1996) and more suitable for development of the immunoassays involving mammalian sera than the parent IgG.

The F(ab')$_2$ antibody fragment, however, has not found widespread use in clinical immunodiagnostic kits as one might expect. This may be attributed to the difficulties and cost-ineffectiveness of large scale production of the F(ab')$_2$ fragments, which is conventionally made by pepsin digestion of IgG and subsequent purification via chromatography.

Ducks and their phylogenetically close relatives and some reptiles, such as turtles, have three kinds of serum immunoglobulins: a macromolecular immunoglobulin IgM (800 kDa in duck), and two isoforms of low molecular weight IgG with sedimentation coefficients of 7.8 S (in duck, 180 kDa) and 5.7 S (in duck, 130 kDa), respectively. (E. R. Unanue et al., *J. Exp. Med.* 121:697-714, 1965; H. M. Grey, *J. Immunol* 98:811-819, 1967; and B. Zimmerman et al., *Biochemistry* 10:482-448, 1971). Avian IgG is oftentimes called IgY due to their existence in egg yolk besides in sera. The 5.7 S IgY, constituted with shorter heavy chains, is structurally and antigenically similar to the F(ab')$_2$ fragment of the 7.8 S IgY (FIG. 1), and this fact leads to the nomenclature of IgY (equivalent to 7.8 S IgY) and IgY($\Delta$ Fc) (equivalent to 5.7 S IgY) to represent both isoforms of IgY (K. E. Magor et al., *J. Immunol.* 149:2627-2633, 1992).

Studies conducted in the infected or experimentally immunized birds showed that duck antibodies are deficient in a number of biological effector functions, including complement fixation and Fc receptors binding, without sacrificing their binding activity to corresponding antigens (G. W. Litman et al., *Immunochemistry* 10:323, 1973; and T. E. Toth et al., *Avian Dis.* 25:17-28, 1981). This may reasonably result from the apparent lack of Fc-equivalent region of the IgY($\Delta$ Fc) antibody that constitutes the quantitatively major component of anseriform bird antibody response. It is thus believed that the IgY($\Delta$ Fc) antibody, which appears to be a structural and functional analog of the F(ab')$_2$ fragment, would provide magnificent advantages in immunological uses, if a promising process for manufacturing the antibody could be found, and the appropriate physical requirements for its activity could be identified.

Avian yolk antibodies have been reported to exhibit useful properties for both research and clinical applications as mammalian antibodies do (see, for example, U.S. Pat. No. 5,340,923; U.S. Pat. No. 5,585,098; U.S. Pat. No. 5,601,823; and U.S. Pat. No. 5,976,519). Egg yolks derived from a laying hen is inexpensive and more convenient and safer to handle as compared to the hyperimmunized mammalian sera. More importantly, yolk antibodies are able to stand up to the scrutiny under modern animal protection regulations (A. Poison et al., *Immunol. Commun.* 9:475, 1980; and B. Gottstein et al.). These facts suggest a potential use of egg yolk as a commercial source of antibodies.

However, high contents of lipidic substances, such as fatty acids, cholesterol and lecithin, in egg yolk make the isolation of yolk antibodies a cumbersome and laborious task. Many efforts have been made in this regard. For instance, water soluble precipitants, including agar, pectin (Japanese Kokai No. 64-38098 published in Feb. 8, 1989), dextran sulfate (J. C. Jensenius et al., *J. Immunol. Methods* 46:63, 1981), natural gums (H. Hatta et al., *J. Food Science* 53:425, 1988) and polyethylene glycol (PEG) (A. Poison et al., *Immunol. Invest.* 14:323, 1985; see also U.S. Pat. No. 4,550,019 issued to A. Poison) were used to precipitate non-aqueous bio-molecules, mainly lipids and yolk granules, to thereby harvest a water soluble phase containing abundant yolk antibodies of the entire population. A. Hassl et al. developed a two-step chromatographic process, comprised of hydrophobic interaction chromatography and size exclusive chromatography, for further isolation of yolk antibodies of the entire population from a PEG-purified fraction (A. Hassl and H Aspock, *J. Immunol. Methods* 110:225, 1988). Akita et al described an improved method for isolating IgY, in which yolk antibodies were extracted from chicken eggs by diluting the egg yolks with a large volume of water and subjecting the resultant supernatant to size exclusive chromatography and/or ion exchange chromatography (E. M. Akita et al., *J. Immunol. Methods.* 160:207, 1993; and E. M. Akita and S. Nakai, *J. Food Sci.* 57:629, 1993).

However, all these studies and patents focus on the isolation of the entire population of yolk antibodies (which at least includes IgY present or absent Fc region) from avian eggs, rather than on the purification of IgY($\Delta$ Fc) and IgY antibodies selectively. Moreover, since IgY($\Delta$ Fc) antibodies are present only in birds belonging to the Order *Anseriformes*, including duck and goose, and since the lipid content in the egg yolk of the anseriform birds is reported higher than that in the galliform birds, such as chicken and turkey, the conventional methods described above provide no suggestion of a successful purification of IgY($\Delta$ Fc) antibody. IgY($\Delta$ Fc) antibody was only purified by co-precipitating with IgY from duck serum (D. A. Higgins et al., *Veterinary Immunology and Immunopathology* 41:169-180, 1995) with complexes and expensive procedures, but still no IgY($\Delta$ Fc) antibody alone was selected isolated from egg yolk.

Therefore, there exists a need for a rapid, cost-effective and high-throughput process that provides easy isolation of the desired IgY antibody from the antibody pool of anseriform bird egg while maintaining the activity of the IgY antibody. The substantially purified IgY($\Delta$ Fc) antibody may acts as a new type of F(ab')$_2$ antibody for various immunodiagnostic and immunotherapeutic uses.

SUMMARY OF THE INVENTION

An extensive research has been conducted to fulfill the industrial requirements for yolk antibodies as indicated above. It is unexpectedly found that a successful isolation of yolk antibodies from egg yolks of an anseriform bird can be readily accomplished through an adsorption chromatographic procedure using a porous water insoluble non-charged adsorbent, and/or through a simple salting-out procedure that differentiates different isoforms of the yolk antibodies. According to the process of the present invention, the highly purified yolk antibodies, in particular the highly purified IgY($\Delta$ Fc), can be easily obtained with high yield in an economic manner, and are ready for a wide variety of immunological uses.

Accordingly, an object of the present invention is to provide a process for selectively isolating IgY antibodies from egg yolk of an anseriform bird, which is characterized in:

(a) adsorbing IgY antibodies in a water-miscible fraction obtained from the egg yolk of an anseriform bird with a porous water insoluble non-charged adsorbent selected from the group consisting of silicate, silicon compounds, carbonate, sulfate, phosphate, carbon, cellulose and synthetic fiber, ceramics, and metal oxide, and wherein the porous water insoluble non-charged adsorbent is at an amount effective for separating the yolk antibodies from the water-miscible fraction; and (b) flowing the porous water insoluble non-charge adsorbent with a buffer to obtain an aqueous fraction containing the IgY antibodies, wherein the IgY antibodies comprise antibodies with Fc regions and antibodies that lack Fc regions.

Another aspect of the invention is to provide a process for selectively isolating IgY antibodies from egg yolk of an anseriform bird, which is characterized in performing first salting out by salting out an aqueous fraction containing yolk antibodies with $(NH_4)_2SO_4$ of a first concentration ranging from about 15% (w/v) to about 24% (w/v), and wherein preferably not more than about 21% (w/v) based on the volume of the aqueous fraction, and then performing second salting out by salting out the aqueous fraction containing yolk antibodies treated in the first salting out with $(NH_4)_2SO_4$ of a second concentration ranging from about 25% (w/v) to about 40% (w/v), and wherein preferably not more than about 31% (w/v) based on the volume of the aqueous fraction treated in the first salting out.

Still another aspect of the invention is to provide a process for selectively isolating IgY antibodies from egg yolk of an anseriform bird, which is characterized in:

(a) adsorbing IgY antibodies in a water-miscible fraction obtained from the egg yolk of an anseriform bird with a porous water insoluble non-charged adsorbent selected from the group consisting of silicate, silicon compounds, carbonate, sulfate, phosphate, carbon, cellulose and synthetic fiber, ceramics, and metal oxide, and wherein the porous water insoluble non-charged adsorbent is at an amount effective for separating the yolk antibodies from the water-miscible fraction;

(b) flowing the porous water insoluble non-charged adsorbent with a buffer to obtain an aqueous fraction containing the IgY antibodies;

(c) salting out the aqueous fraction containing IgY antibodies in step (b) with $(NH_4)_2SO_4$ of a first concentration ranging from about 15% (w/v) to about 24% (w/v), and wherein preferably not more than about 21% (w/v) based on the volume of the aqueous fraction; and (d) salting out the aqueous fraction containing IgY antibodies treated in step (c) with $(NH_4)_2SO_4$ of a second concentration ranging from about 25% (w/v) to about 40% (w/v), and wherein preferably not more than about 31% (w/v) based on the volume of the aqueous fraction treated in step (c); wherein the IgY antibodies comprise antibodies with Fc regions and antibodies that lack Fc regions.

According to the process of this invention, an abundant amount of a selected isoform of yolk antibodies, in particular IgY($\Delta$ Fc) antibody, available for various industrial applications can be obtained in an economic, efficient and time-saving manner.

It is still another object of the invention to provide the clinical and research uses of the IgY antibody so produced. In addition to the cost-effectiveness and ease of preparation, the IgY($\Delta$ Fc) antibody according to the present invention has advantages of being inactive to the complement system and rheumatoid factors in mammalian sera, and having poor cross-reactivity to mammalian IgG, and is thus particularly suitable for use in immunological assays involving mammalian sera with minimal interference. It would be appreciated by those skilled in the art that the IgY antibody can be present in the form of a single reagent for clinical, research and other applications, or included in a commercial kit as an active component.

It is another specific object of the invention to provide a reagent for immunoassay of an etiological agent of interest, comprising an IgY antibody obtained by the process according to this invention.

BRIEF DESCRIPTION OF THE DRAWINGS

The above and other objects and features of the present invention will become apparent with reference to the following description of the preferred embodiments taken in conjunction with the accompanying drawings, in which:

FIG. 5 illustrates a SDS-PAGE analysis comparing the antibody adsorption abilities of the adsorbents.

FIG. 6 illustrates a SDS-PAGE analysis comparing the antibody adsorption abilities of the fumed silica.

DETAILED DESCRIPTION OF THE INVENTION

Figure 1:
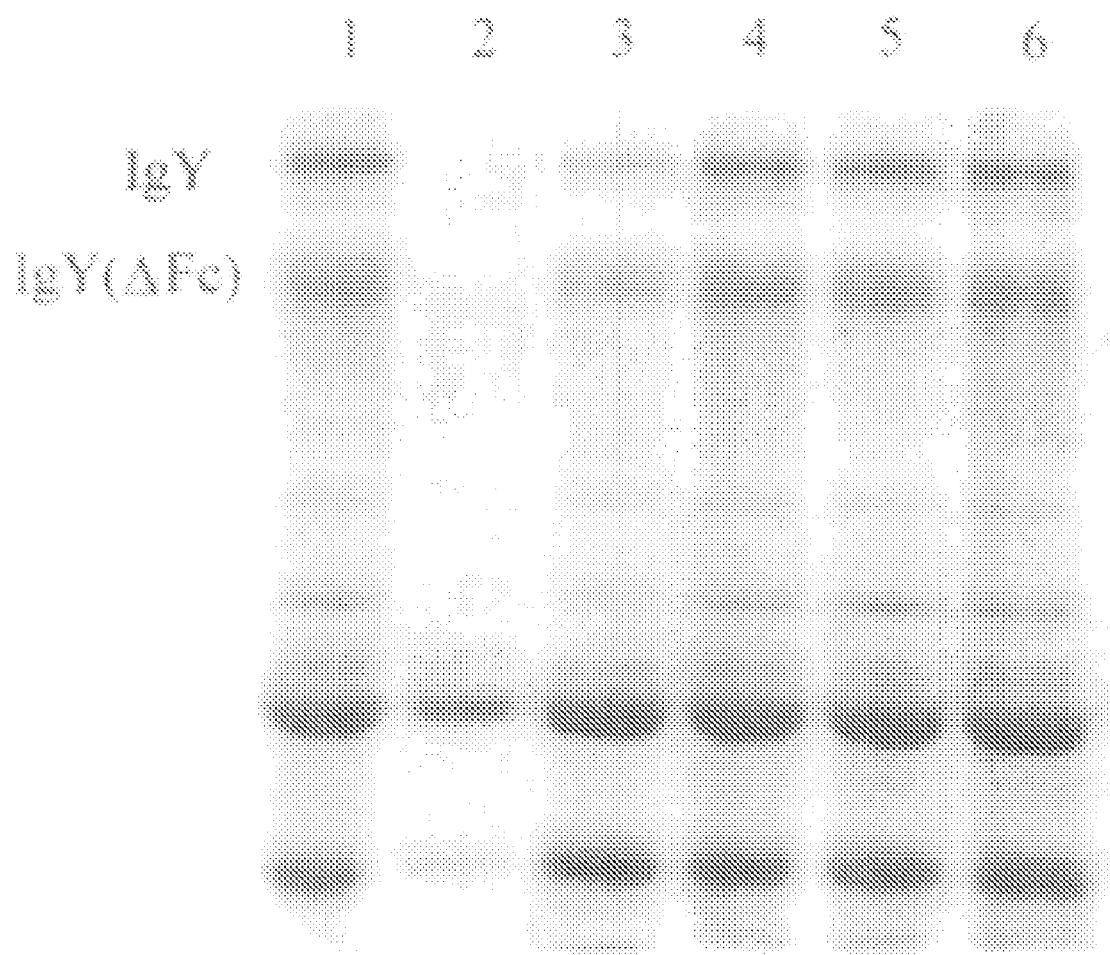
FIG. 1 illustrates a SDS-PAGE analysis comparing the antibody adsorption abilities of four adsorbents: lane 1, the partially purified antibody extract; lane 2, the solution flowing through 2% fumed silica; lane 3, the solution flowing through 3% silica dioxide; lane 4, the solution flowing through 3% Celite® diatomite; lane 5, the solution flowing through 3% Celite® diatomite hyflo-Cel; and lane 6, the solution flowing through 5% Celite® diatomite hyflo-Cel.

The IgY antibodies are abundant in the bird serum and the eggs laid by the bird. However, as described above, collection of the antibody from the egg is usually preferred on account of the cost. The laying hen transfers both of the IgY and IgY(Δ Fc) isoforms from serum to the egg yolk. In principle, each duck egg contains about 1 to about 4 mg IgY/ml and about 3 to about 12 mg IgY(Δ Fc)/ml in the yolk and, therefore, the total quantity of the antibodies contained in a single egg is estimated to be 15 to 80 mg of IgY and 45 to 240 mg of IgY(Δ Fc). The large volume of egg yolk produced vastly exceeds the volume of the serum that can be safely obtained from the birds over any given time period. In addition, extraction of yolk antibodies can be performed on a large scale without costly investment. Preferably, antibodies in the present invention are obtained from eggs of an anseriform bird immunized with a specific antigen.

In accordance with the present invention, it provides a process for efficiently isolating antibodies from egg yolk, in which the so-called "adsorption chromatography" or "differential salting-out," which may be used alone or in combination with the other, acting as critical steps in the isolation.

As used herein, the term "adsorption chromatography" is directed to a type of separation method involving the use of a stationary phase to selectively take up and concentrate the desired solutes from a mobile phase. According to one aspect of the present invention, a porous water insoluble non-charged adsorbent acts as the active constituent in the stationary phase to separate the yolk antibodies by adsorbing the yolk antibodies in the porous water insoluble non-charged adsorbent accompanied with trapping water-miscible lipidic impurities normally present in egg yolk. The porous water insoluble non-charged adsorbent according to the invention has an enormous surface area that is taken as an index for representing the pore size and pore distribution of the porous water insoluble non-charged adsorbent according to the invention. The inventor found that the IgY antibodies can be adsorbed into the pore of the porous water insoluble non-charged adsorbent according to the invention, and the antibodies are able to be separated from water-miscible lipidic impurities and other proteins. Preferably, the surface area of the porous water insoluble non-charged adsorbent according to the invention ranges from about 0.0005 $m^2/g$ to about 8 $m^2/g$; more preferably, from about 0.1 $m^2/g$ to about 2 $m^2/g$. In general, a porous water insoluble non-charged adsorbent with a larger specific surface area is able to adsorb more IgY antibodies than that with a less specific surface area.

The specific surface area can be measured directly. For example, gas adsorption technique is well developed in measuring the specific surface area. One or more data points of the adsorption isotherm are measured and the BET (Brunauer, Emmett and Teller) equation is used to give specific surface area from this data. The particle size and density are related to specific surface area. In general, an adsorbent having a larger particle size or density has a smaller specific surface area.

The amount of the porous water insoluble non-charged adsorbent effective for separating the IgY antibodies from the water-miscible fraction is relevant to the specific surface area thereof. For example, the particle size of Celite® diatomite hyflosupercel is smaller than that of Celite® diatomite. Therefore, the specific surface area of Celite® diatomite hyflosupercel is much larger than that of Celite® diatomite. It is found that the adsorbability of Celite® diatomite hyflosupercel is better than Celite® diatomite (referring to FIGS. 8a and 8b). The suitable amount of the porous water insoluble non-charged adsorbent with a given specific surface area can be quickly determined through a simple and quick test as illustrated in the Example in the invention. Usually, the amount of a porous water insoluble non-charged adsorbent with a larger specific surface area is less than that with a smaller specific surface area for adsorbing the same quantity of IgY antibodies.

In a preferred embodiment of the present invention, the yolk is firstly separated from the egg white, and then washed with distilled water to remove as much albumen as possible. The vitelline membrane encapsulating the yolk is punctured, and the separated yolk fraction is then diluted with an effective amount of an aqueous buffer or water to form a suspension of the egg yolk. Preferably, the collected egg yolk is diluted with an aqueous buffer solution or distilled water ranging from about 2 parts to about 40 parts by volume, more preferably from about 5 parts to about 30 parts by volume, per 1 part of the egg yolk. Value of pH is reported to be a critical factor during the stage of partial purification (E. M. Akita and S. Nakai, *J. Food Sci.* 57:629, 1993). For the best recovery of yolk antibodies, pH is preferably set within a range of about 5 to about 7. Desirably, the temperature in this step is within a range of about 0° C. to about 60° C. The suspension of the egg yolk is gently agitated to form a homogenous mixture, and then allowed to stand for a period of time sufficient to form the aqueous and non-aqueous phases. The porous water insoluble materials, including non-aqueous bio-molecules such as lipoproteins, phospholipids, sterols and the like, are then removed from the aqueous yolk suspension by centrifugation. The resulting antibody-containing supernatant may then be separated from the viscous precipitant by decanting, suctioning, or other like methods known in the art.

In general, the lipid content of the water-miscible fraction thus obtained is still so high as to be adverse to the subsequent manipulation. According to the present invention, a stationary phase containing a porous water insoluble non-charged adsorbent is incubated with the water-miscible fraction in a sufficient amount to adsorb the yolk antibodies and to adsorb the majority of the water-miscible lipidic substances remaining in the water-miscible fraction. The suitable adsorbents include but are not limited to silicate, silicon compound, carbonate, sulfate, phosphate, carbon, cellulose and synthetic fiber, ceramics, and metal oxide, and wherein the silicate includes synthetic or natural clays, kaolin, talc, and calcium silicate; the silicon compound includes fumed silica, amorphous silica, silica dioxide, silica gel, silicates, diatomaceous earth, and Fuller's earth; carbonate includes calcium carbonate and barium carbonate; sulfate includes calcium sulfate; phosphate includes calcium phosphate; carbon includes activated carbon and carbon fiber, cellulose and synthetic fiber includes cellulose powder; and metal oxide includes aluminum oxide and titanium oxide. Particularly preferred adsorbents are fumed silica, silica dioxide and diatomaceous earth. The working ratio of the adsorbent to the water-miscible fraction can vary over a wide range depending upon the properties of the adsorbent chosen. When fumed silica is used in this process, it is preferably added to a concentration of equal to or higher than about 0.1% by weight, and more preferably ranged between about 0.3 to about 5.0% by weight, based on the volume of the water-miscible fraction to be treated. When the adsorbent is silica dioxide or diatomaceous earth, the adsorption chromatography according to this invention is preferably carried out at more than about 1% by weight, and more preferably in a range of about 3 to about 20% by weight, of the adsorbent based on the volume of the water-miscible fraction to be treated.

The adsorption chromatography according to this invention can be effectuated by any conventional ways, such as batch treatment of the water-miscible fraction with an adsorbent or flowing the water-miscible fraction over a chromatography column packed with the adsorbent, as long as the amount of the yolk antibodies retained on the surfaces of the adsorbent is satisfactory. The reaction time and temperature during the treatment are not critical to the results, and a reaction temperature of about 4 to about 30° C. and a reaction time of about 10 to about 60 minutes are usually feasible. While the adsorption procedure can be repeated several times, each with fresh adsorbent, if necessary, a single operation is normally sufficient. By way of this procedure, the lipids and most of the non-lipid substances can be successfully separated into two immiscible phases while yolk antibodies can also be adsorbed.

Depending upon the capability of the selected adsorbent to capture immunoglobulins, the yolk antibodies can be recovered from either an eluate eluted from the stationary phase or the "flow-through solution" which, as used herein, is intended to represent the solution passing through the stationary phase. As shown in the preferred embodiments given in the text, the yolk antibodies are mainly present in the stationary phase when fumed silica or silica dioxide is used as the adsorbent, whereas diatomaceous earth leaves more than about 60% of the antibodies in the flow-through solution.

The choice of a particular method to obtain yolk antibodies can be determined by the skilled artisan. Typically, the yolk antibodies are obtained in an aqueous fraction by flowing the porous water insoluble non-charged adsorbent with a buffer, and wherein the buffer is at a pH of lower than about 4 or higher than about 8 or containing a chaotropic agent can be utilized in the present invention to obtain the yolk antibodies from the stationary phase without substantially dissociating the lipidic substances from the stationary phase, such that an antibody-containing eluate is formed. As used herein, the term "eluate" is directed to a solution containing the desired substances unbound by the eluent from the stationary phase. The term "chaotropic agent" or "chaotrope" is directed to a chemical capable of inducing a conformational change in a protein molecule, such as an antibody molecule, which is therefore often known as a protein denaturant. According to the invention, most of the bound antibodies can be successfully eluted with any neutral buffer containing moderate concentration (>0.1 M) of a chaotropic agent. In most instances, removal of the chaotrope after elution will restore the native protein structure.

The useful buffer include but are not limited to 0.1 M glycine-HCl, pH 2.3; 0.1 M glycine-HCl, pH 10.0; 3 M to 6 M guanidine-HCl, pH 3.0; 3.0 M potassium chloride; 5 M potassium iodide; 3.5 M magnesium chloride; 0.1-3 M ammonium/sodium/potassium thiocyanate and 6 M urea. With respect to the activity of the recovered antibodies, however, a moderate-ionic strength, chaotrope-containing, neutral pH buffer, such as 3 M sodium thiocyanate buffered in 20 mM MES buffer (pH 5.8) or 20 mM Tris(hydroxymethyl)-aminomethane (pH 7.5), is more suitable for practicing the invention. The active state of the collected antibodies can be easily restored by, for example, extensive dialysis against a low-ionic strength, non-chaotrope-containing, and weakly acidic buffer.

According to one aspect of the present invention, the aqueous fraction including the eluate or the flow-through solution, which is enriched with antibodies, can subsequently be subjected to a procedure of differential salting-out to separate yolk antibody isoforms.

The term "salting-out" as used herein takes on its common meaning in the art of protein chemistry and is directed to the addition of a non-denaturing salt or salts to a mixture or production batch to decrease the solubility of proteins, which leads to the precipitation or coagulation of the proteins. By the term "differential salting-out" is meant a salting-out process that differentially precipitates or coagulates two or more proteins from a mixture by varying the concentration of the added salt or salts. In the present invention, the proteins intended to be differentially precipitated are the isoforms of yolk antibodies, i.e., IgY and IgY($\Delta$ Fc). Examples of the non-denaturing salts useful for precipitation of the yolk antibodies include but are not limited to NaCl, $Na_2SO_4$, $(NH_4)_2SO_4$, KCl, $CaCl_2$, and $MgSO_4$. Preferably, the non-denaturing salt is $Na_2SO_4$ or $(NH_4)_2SO_4$, and $(NH_4)_2SO_4$ is the most preferred. The salt concentration for differentially precipitating yolk antibody isoforms depends on the type of the salt and can be determined by a skilled artisan through simple tests. According to a preferred embodiment of the present invention, in which $(NH_4)_2SO_4$ is employed, IgY is firstly salted out at a concentration ranging from about 15% (w/v) to about 24% (w/v), preferably equal to or lower than about 21% (w/v), of the salt on the basis of the treated volume of the aqueous fraction, while IgY($\Delta$ Fc) is precipitated as the concentration of the salt ranging from about 25% (w/v) to about 40% (w/v), preferably about 31% (w/v) based on the treated volume of the aqueous fraction. It should be appreciated that the sequence of precipitation of the two antibody isoforms could be also variable depending on the salt chosen. The combined use of two or more salts in this procedure, e.g., firstly precipitating a first isoform with one salt followed by precipitating a second isoform with another salt, is also feasible. The differential salting-out procedure according to the present invention dramatically accomplishes a main object of the present invention, i.e., essential selectively separation of the desired IgY comprising IgY and IgY($\Delta$ Fc) antibodies from the whole population of yolk antibodies constituted by both IgY and IgY($\Delta$ Fc).

If obtaining the antibodies with a higher purity is desired, the precipitated antibodies can be re-dissolved in a suitable buffer system and subjected to additional purification procedures, such as size exclusive chromatography, hydrophobic interaction chromatography, ion-exchange chromatography and immuno-affinity chromatography.

As used herein, the term "immunoaffinity purification" or "immunoaffinity chromatography" is directed to a type of separation method based on the binding characteristics of antibodies for a specific antigen. That is, the antibodies that bind to a specific antigen under a particular condition are separated from the unbound antibodies under that condition. The present invention contemplates the use of immunoaffinity purification to eliminate irrelevant proteins, in particular the non-antigen-binding immunoglobulin.

According to the present invention, the immunoaffinity purification is conducted by use of an "antigen matrix" comprised of antigen immobilized onto an insoluble support. The type of the support is not critical to the immunoaffinity purification of the invention. Any conventional support material suitable for the covalent attachment of an antigen and inert to the interaction between the desired antibody and the antigen immobilized thereon is useful. Usually, the support is made of crosslinked agarose or crosslinked dextran, such as the CNBr-activated Sepharose 4B commercially available from Pharmacia.

The antibodies purified by differential salting-out is dissolved in a "binding buffer" and applied onto the antigen matrix, so that the immuno-complexes of the immobilized antigens and the yolk antibodies are formed. Any buffer system inert to the antigen-antibody interaction and effective to maintain the desired binding condition is useful in the present invention. Preferably, the binding buffer is selected from the group consisting of a phosphate buffer, an MES (2-[N-morpholino]ethanesulfonic acid) buffer and a bis-Tris buffer, among which an MES buffer at a concentration of 20 mM is the most preferred.

Preferably, the immunoaffinity purification is conducted in an environment of weak acid and low ionic strength, i.e., at pH within a range of about 4 to about 7 and under an ionic strength of lower than about 50 mM. More preferably, the antibodies were allowed to interact with the immobilized antigen at pH within a range of about 5 to about 6 and most preferably within a range of about 5.6 to about 5.8. The yolk antibodies can be dissociated from the antigen matrix by a chaotropic salt, or at a pH of lower than about 4 or higher than about 8. The activity of the collected antibodies can be restored by, for example, extensive dialysis against a low-ionic strength, non-chaotrope-containing, weakly acidic buffer.

The purified IgY($\Delta$ Fc) according to the process of the invention neither activate the complement system nor binds to rheumatoid factor of mammalian sera. The immunological cross-reactivity between IgY($\Delta$ Fc) and the mammalian IgG is not significant. Thus, the invention also provide a new type of antibody suitable for clinical and research uses.

The invention also provides a broad variety of clinical and research uses of the IgY antibody prepared according to the invention.

For example, the present invention provides a pharmaceutical composition for treating or prophylaxis an animal (which includes domestic fowls, livestock and companion animals) or human patient comprising a therapeutic amount of the IgY antibody of the present invention for protecting or prophylaxis them from various etiological agents, including microorganisms, such as bacteria, native, recombinant or peptide-synthetic viruses, fungi, protozoa, nematodes and the like, and proteinaceous or non-proteinaceous substances, such as native, recombinant or peptide-synthetic allergens, toxins, venoms, hormones or any other immunogen capable of eliciting an immune response. Preferably, the purified IgY antibody is applied in combination with a pharmaceutically acceptable carrier such as water, saline and the like. The pharmaceutical composition can be delivered by ways comprising oral delivery, injection, external administration, and immunizing treatment.

The IgY antibody of the present invention is also useful for detecting an etiological agent of interest, including, for example, a pathogenic or non-pathogenic organism, such as *Escherichia coli, Salmonella enterititis*, and other bacterial organisms; a native, recombinant or peptide-synthetic hormone such as estrogen, progesterone, thyroxin and the like; a major histocompatibility complex antigen and the like; a native, recombinant or peptide-synthetic tumor marker such as alpha-fetoprotein, prostate specific antigen and the like; a disease state marker such as C-reactive protein, ferritin and the like; an accumulation or a residual of foreign materials such as drugs of Theophylline and digoxin; in a body sample such as a fluid, tissue, cell extract and the like, that is derived from the human or animal. In order to obtain antibodies only specific to the etiological agents, the etiological agent can be injected into the ducks as antigens for inducing the production of desired antibodies, and wherein the antigens comprise naturally purified antigens, recombinant antigens, peptide-synthetic antigens, and plasmid DNA. Using the IgY antibody obtained according to this invention, an etiological agent of interest can be quantitatively or qualitatively detected by any conventional method known in the art, such as the Ouchterlony double diffusion methods (ODD), the single radial immuno diffusion method (SRID), the immuno electrophoresis method (IEP), the radioimmuno assay method (RIA), the enzyme-linked immuno sorbent assay method (ELISA), the Western blot method (WB), the turbidimetric immunoassay method (TIA), the particle-enhanced turbidimetric immunoassay method, an enzymatic immunoassay, a nephelometric immunoassay, a chemiluminescent immunoassay, an immuno gold assay, or an immuno-chromatography assay.

The IgY antibody of the present invention is also adapted for use in biochips and biosensors.

The following Examples are given for the purpose of illustration only and are not intended to limit the scope of the present invention.

Example 1

Immunization Procedure for Stimulation of Specific Antibody Production

Twelve, 16-week old, domestic ducks (*Anas platyrhynchos* var. *domestica*) were individually housed for antibody and egg production. The ducks received an initial subcutaneous injection of 1-5 mg/ml of human C-reactive protein (CRP; purified from human ascites) in phosphate buffer, pH 7.5 emulsified with an equal volume of complete Freund's adjuvant. The concentration of the antigen used was generally in the range of 1 to 5 mg/ml. After the initial injection, young hens received three additional injections of 1-5 mg of antigen every two weeks. One week later, eggs began to be collected, labeled and stored at 4° C. until processed for extraction and purification of antibody. The booster procedure was repeated every four weeks during the experiment. Blood was sampled at the seventh day after each booster injection. Each blood sample was centrifuged and the resulting serum was collected.

Example 2

Extraction of Antibodies from Duck Yolks

The yolks collected from the eggs laid by the hyperimmunized ducks of Example 1 were thoroughly washed by a weak jet of distilled water, to thereby remove albumen. The volume of yolk was measured and then mixed thoroughly with distilled water in an amount of ten times the measured amount of yolk. The mixture was then held for at least two hours under 4° C., and subsequently centrifuged at 10,000 rpm in a Hitachi® CR-22F centrifuge for one hour. A pale supernatant layer and a semi-solid pliable layer were formed in centrifuge tubes.

Example 3

Treatment with Adsorbents

To the crude extract prepared in Example 2 were added with one of the adsorbents: 2% (w/v) fumed silica (purchased from Sigma), 3% (w/v) silica dioxide (sigma), 3% (w/v) Celiteg diatomite (purchased from Celite® Corporation), and 3 or 5% (w/v) Celite® diatomite hyflo-Cel (Celite® Corporation). The resultant suspensions were incubated at 4° C. for 60 minutes with gentle stirring. After completion of the incubation, the adsorbents were precipitated at 4° C. at higher than 5,000 rpm in a Hitachi® CR-22F centrifuge, and the supernatants and pellets were harvested separately. Ten µl samples taken from each supernatant were subjected to non-reducing sodium dodecyl sulfate polyacrylamide gel electrophoresis (SDS-PAGE).

As shown in FIG. 1, in terms of the quantity of the antibodies adsorbed by the adsorbents, fumed silica has the best adsorption activity and almost no antibody was left in the flow through solution.

Silica dioxide displays a slightly weaker affinity to immunoglobulins, which perhaps results from its larger particle size (and thus comprising a less surface area) than fumed silica. On the other hand, less than 10% of the yolk antibodies were captured by either type of the diatomaceous earths.

Example 4

Differential Salting-Out of Yolk Antibodies

Figure 2:
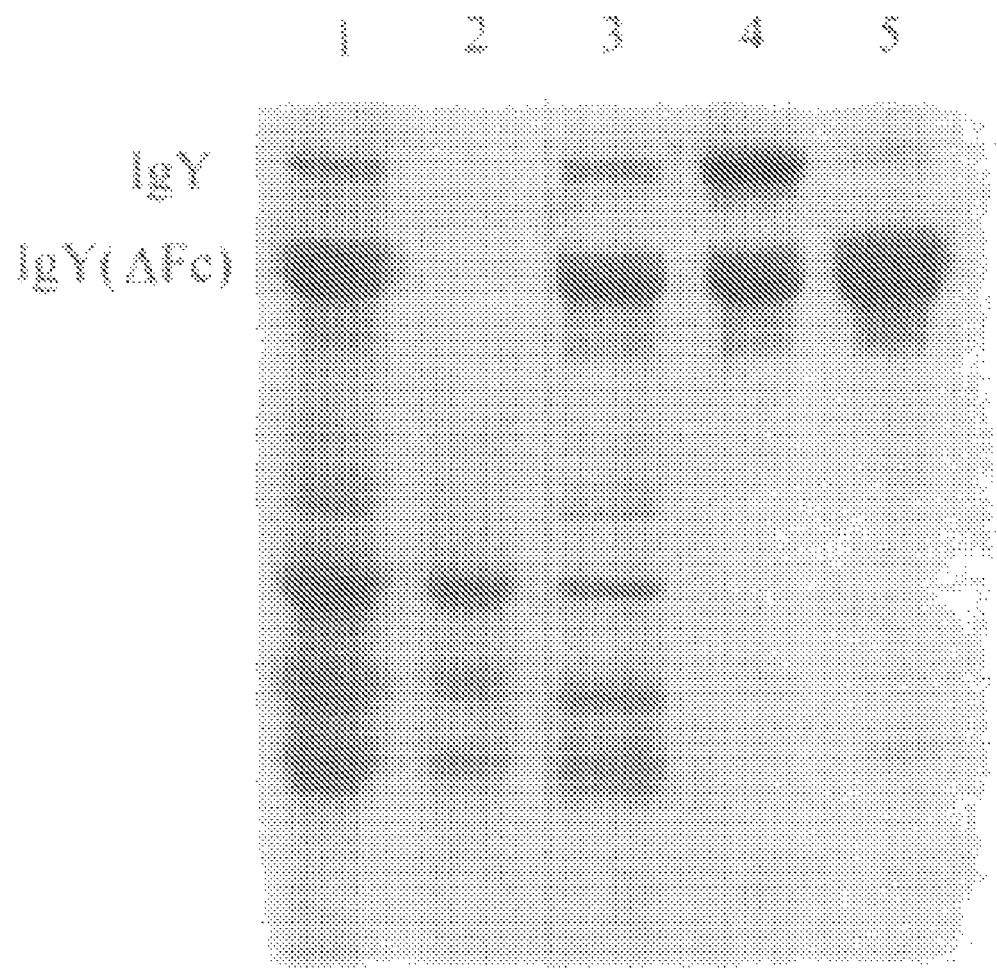
FIG. 2 illustrates the electrophoresis results of the purified yolk antibodies using fumed silica as the adsorbent run on an 8% SDS-polyacrylamide gel: lane 1, the partially purified antibody extract; lane 2, the solution flowing through 2% fumed silica; lane 3, the eluate from the fumed silica pellet; lane 4, the antibody product precipitated with 21% (w/v) ammonium sulfate in the first precipitation step; and lane 5, the antibody product precipitated with 31% (w/v) ammonium sulfate in the second precipitation step.

The fumed silica pellet obtained in Example 3 was treated with 2.5 M sodium thiocyanate (pH 7.5) to elute the antibodies bound thereon. The resultant eluate was firstly precipitated with ammonium sulfate at a concentration of about 21% (w/v) based on the volume of the eluate, followed by a second precipitation with addition of ammonium sulfate to about 31% (w/v). The precipitated antibody products were re-dissolved in phosphate buffer saline (PBS). Analytical SDS-PAGE was performed on a 8% non-reducing acrylamide gel, in which 2237 µg of the crude extract of example 2 (lane 1), 10 µl of the flow through harvested in Example 3 (lane 2), 1122.25 µg of the eluate from the fumed silica pellet (lane 3), and 153 µg and 372.85 µg of the antibody products obtained in the first and second precipitation steps (lane 4 and lane 5, respectively) were loaded. The result is shown in FIG. 2. The percentage recovery and purity were determined by scanning densitometry of the gel and summarized in Table 1.

TABLE 1

|  | Total protein | IgY percentage | IgY yield/egg | IgY($\Delta$ Fc) percentage | IgY($\Delta$ Fc) yield/egg |
|---|---|---|---|---|---|
| Crude extract | 447.4 mg | 4.43% | 19.82 mg | 26.79% | 119.86 mg |
| Eluate | 224.45 mg | 8.15% | 18.29 mg | 41.65% | 93.48 mg |
| $1^{St}$ precipitation by 21% $(NH_4)_2SO_4$ | 30.65 mg | 37.82% | 11.59 mg | 62.18% | 19.06 mg |
| $2^{nd}$ precipitation by 31% $(NH_4)_2SO_4$ | 74.57 mg | 2.03% | 1.51 mg | 96.62% | 72.05 mg |

As illustrated in Table 1, the resulting IgY(Δ Fc) antibodies are recovered in about 76% yield (72.05 mg/119.86 mg×100%) in greater than 96% purity. More importantly, this purification scheme advantageously leads to the essential separation of the desired IgY(Δ Fc) antibodies from the whole population of yolk antibodies constituted mainly by both IgY and IgY(Δ Fc).

Example 5

Partially Purified IGY(Δ Fc) with Celite® Diatomite

Figure 3:
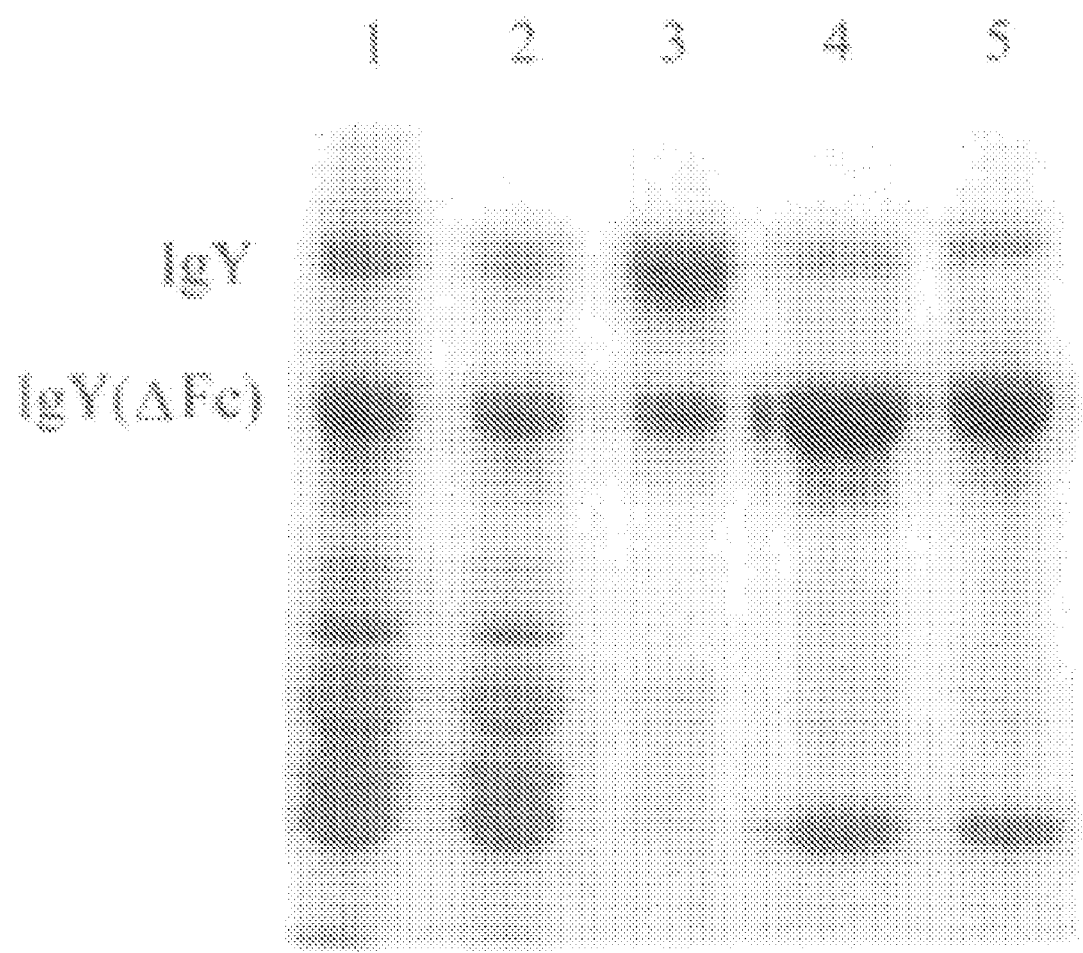
FIG. 3 illustrates the electrophoresis results of the purified yolk antibodies using Celite® diatomite as the adsorbent run on an 8% SDS-polyacrylamide gel: lane 1, the partially purified antibody extract; lane 2, Celite diatomite filtrate; lane 3, the antibody product precipitated with 21% (w/v) ammonium sulfate in the first precipitation step; lane 4, the antibody product precipitated with 31% (w/v) ammonium sulfate in the second precipitation step; and lane 5, the antibody product precipitated with 16% (w/v) sodium sulfate in the second precipitation step.

Taking advantage of the ability of diatomaceous earth to attract lipids and repulse antibodies, the crude extract prepared in Example 2 was poured onto a filtration column packed with 10% by weight of Celite diatomite based on the poured volume of the extract. The solution flowing through the column was harvested and subjected a first precipitation with 21% (w/v) ammonium sulfate based on the volume of the flow through solution. The precipitated antibodies were collected and the supernatant was divided into two parts. One part of the supernatant was precipitated with ammonium sulfate at a concentration of about 31% (w/v), while the other part was precipitated with 16% (w/v) sodium sulfate. The precipitated antibody products were re-dissolved in PBS. Analytical SDS-PAGE was performed on a 8% non-reducing acrylamide gel, in which 2012.5 μg of the crude extract of Example 2 (lane 1), 1678 μg of the flow through harvested by Celite diatomite filtration (lane 2), 94.9 μg of the eluate obtained in the first precipitation step (lane 3), and 169.65 μg and 357.75 μg of the antibody products obtained in the second precipitation step by 31% ammonium sulfate and 16% sodium sulfate (lanes 4-5) were loaded. The result is shown in FIG. 3. The percentage recovery and purity were determined by scanning densitometry of the gel and summarized in Table 2.

TABLE 2

|  | Total protein | IgY percentage | IgY yield/egg | IgY(Δ Fc) percentage | IgY(Δ Fc) yield/egg |
|---|---|---|---|---|---|
| Crude extract | 405.2 mg | 11.60% | 46.98 mg | 29.01% | 117 mg |
| CLT filtrate | 335.6 mg | 5.08% | 17.05 mg | 30.47% | 102.25 mg |
| $1^{St}$ precipitation by 21% $(NH_4)_2SO_4$ | 18.98 mg | 62.60% | 11.88 mg | 37.40% | 7.10 mg |
| $2^{nd}$ precipitation by 16% $Na_2SO_4$ | 33.93 mg | 6.29% | 2.13 mg | 77.14% | 26.17 mg |
| $2^{nd}$ precipitation by 31% $(NH_4)_2SO_4$ | 71.55 mg | 8.79% | 6.29 mg | 68.68% | 49.14 mg |

As illustrated in Table 2, the resulting IgY(Δ Fc) antibodies are recovered in about 77% (when sodium sulfate is used in the second precipitation step) and 69% purity (when ammonium sulfate is used in the second precipitation step), respectively, with high yields.

Example 6

Immunoaffinity Purification of Yolk Antibodies

A C-reactive protein (CRP) solution was prepared in 0.1 M carbonate buffer, pH 8.5 at a concentration of 5 mg/ml. CNBr-activated Sepharose 4B purchased from Pharmacia was washed initially with 1 mM cold HCl in an amount of ten times the matrix volume and allowed to react with the CRP solution in an amount of two times the matrix volume of at 4° C. overnight. The antigen matrix was suspended in a solution of 0.5 M ethanolamine in 20 mM Tris-HCl (pH 8.5) in a ratio of 1:1 (v/v) for 2 hours at 4° C. to block remaining protein-reactive sites. The antigen matrix was then washed with PBS containing 0.02% sodium azide and stored at 4° C.

Figure 4:
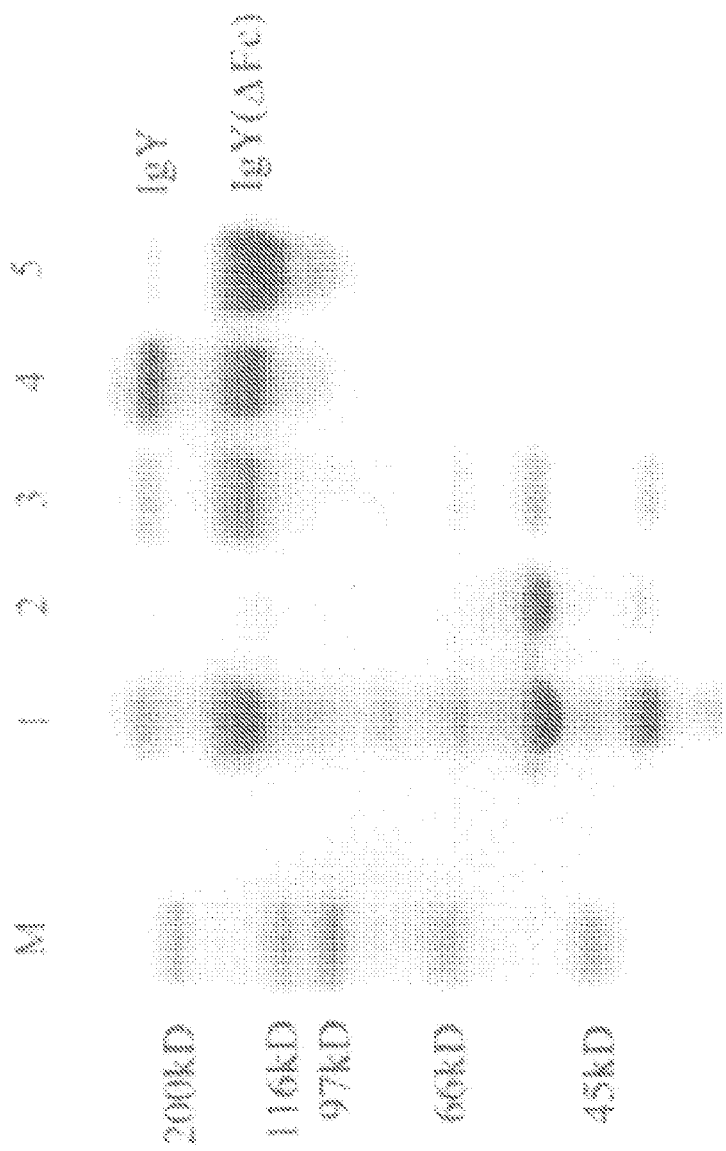
FIG. 4 illustrates the electrophoresis results of the purified yolk antibodies using fumed silica as the adsorbent run on an 8% SDS-polyacrylamide gel: M, molecular weight marker; lane 1, the partially purified antibody extract; lane 2, the solution flowing through 2% fumed silica; lane 3, the eluate from the fumed silica pellet; lane 4, the antibody product precipitated with 21% (w/v) ammonium sulfate; and lane 5, the antibody product purified by affinity chromatography.

The duck antibodies precipitated with 21% (w/v) ammonium sulfate in Example 4 and the antigen matrix prepared above were used. One ml of the antigen matrix was packed into a conventional column and soaked in 20 mM of MES (2-[N-morpholino]ethanesulfonic acid) buffer (pH 5.8). The antigen matrix was allowed to react with 0.25 ml of the antibodies formulated in the same binding buffer. The antigen matrix was washed with the binding buffer until the effluent was substantially free of protein. Bound antibodies were eluted immediately with 6 M guanidine-HCl, and the optical density thereof was measured at 280 nm after a complete dialysis. The SDS-PAGE analysis shown in FIG. 4 indicates that the affinity-purified antibodies are constituted mainly by IgY(Δ Fc) antibody which is represented by a single band on the gel.

Example 7

Porous Water Insoluble Non-Charged Adsorbents

Different porous water insoluble non-charged adsorbents were utilized for assaying the adsorption ability thereof. The assay was carried as described in Example 3. The porous water insoluble non-charged adsorbents assayed were: 2% (w/v) fumed silica (specific surface area: 200±25 m²/g), 5% (w/v) charcoal, activated (56 μm), 5% (w/v) or 10% (w/v) Celite® diatomite (particle size: 48 μm), 5% (w/v) or 10% (w/v) kaolin (particle size: 0.1-4 μm), 5% (w/v) cellulose (Sigmacell™ type 101), 5% (w/v) silicon dioxide (particle size: 1-5 μm), 5% (w/v) silica gel type G (size: 10-40μ), 5% (w/v) or 10% (w/v) silica gel type H (size: 10-40μ), 5% (w/v) or 10% (w/v) Celite® diatomite hyflosupercel (particle size: 27 μm).

Figure 5A:
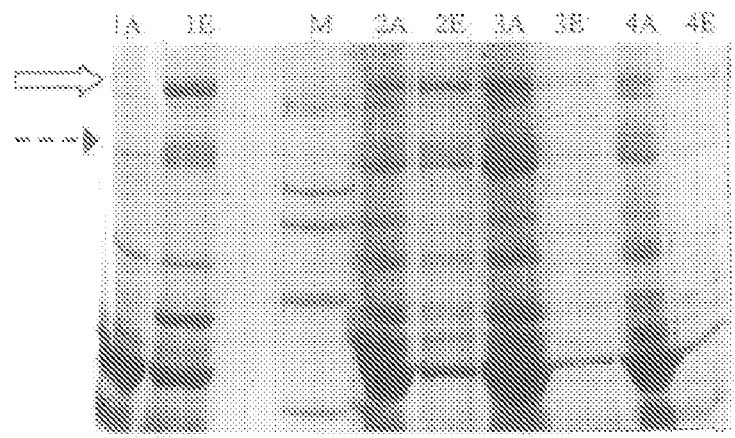
FIGS. 5a and 5b: M: marker; lane 1:2% (w/v) fumed silica; lane 2:5% (w/v) charcoal, activated; lane 3:5% (w/v) Celite® diatomite; lane 4:5% (w/v) kaolin; lane 5:5% (w/v) cellulose (Sigmacell™ type 101); lane 6:5% (w/v) silicon dioxide; lane 7:5% (w/v) silica gel type G; lane 8:5% (w/v) silica gel type H; lane 9:5% (w/v) Celite® diatomite hyflosupercel.
Figure 5B:
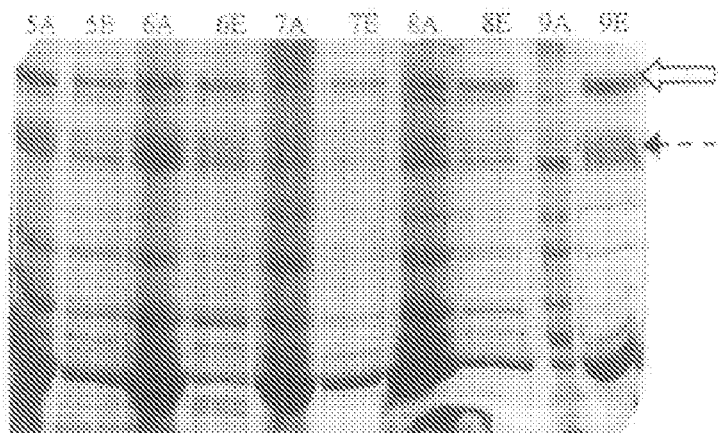
Figure 5C:
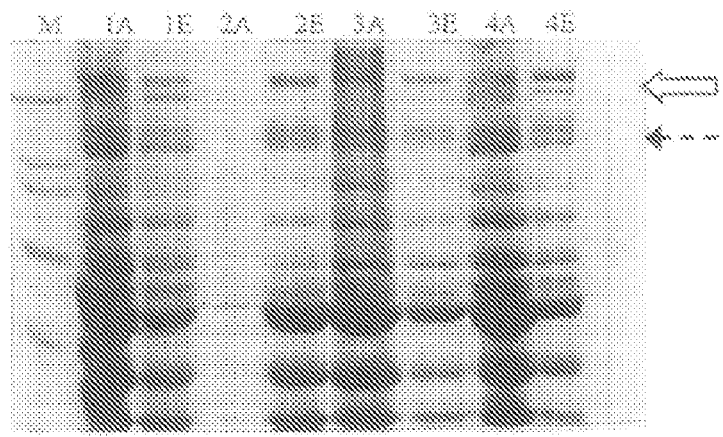
FIG. 5c: lane 1:10% (w/v) Celite® diatomite; lane 2:10% (w/v) kaolin; lane 3:10% (w/v) silica gel type G; lane 4:5% (w/v) silica gel type H; the letter A indicated the flow-through solution of egg yolk extractions after adsorption; the letter E indicated the eluate from the pellet after adsorption; the hollow arrow indicated the position of IgY and the arrow with dotted line indicated the position of IgY(Δ Fc)

The results are shown in FIGS. 5a to c, which evidence that all the adsorbents are able to adsorb IgY antibodies.

Example 8

Specific Surface Area

Fumed silica (0.1, 0.2 and 0.4% (w/v)) with a particle size of 12 nm and specific surface area of 200±25 m²/g, Celite® diatomite (2, 4 and 8% (w/v)) with a particle size of 48 μm and Celite® diatomite hyflosupercel (2, 4 and 8% (w/v)) with a particle size of 27 μm were utilized for illustrating the relationship between the adsorption ability and specific surface area. The assay was carried as described in Example 3.

Figure 6A:
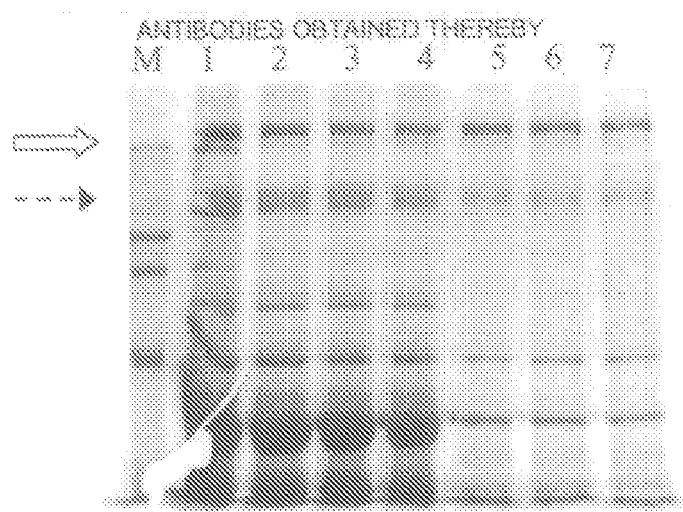
FIG. 6a is 0.1% (w/v)
Figure 6B:
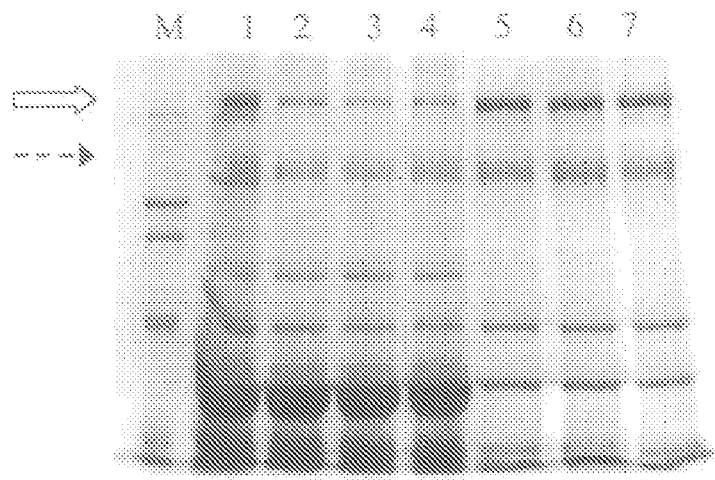
FIG. 6b is 0.2% (w/v)
Figure 6C:
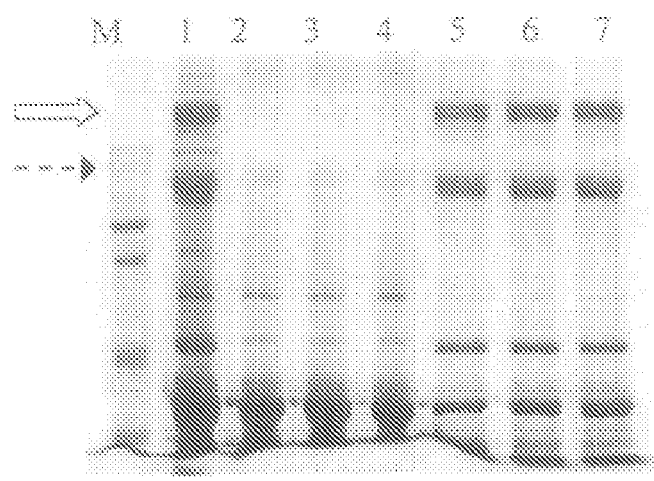
FIG. 6c is 0.4% (w/v); M: marker; lane 1: egg yolk extraction; lanes 2 to 4: flow-through solution; lanes 5 to 7: eluate; the hollow arrow indicated the position of IgY and the arrow with dotted line indicated the position of IgY(Δ Fc)

The result of fumed silica is shown in FIGS. 6a to c. The more adsorbents are used, the more antibodies are adsorbed. It is estimated that the antibodies in the flow-through solution are 19% (0.1% w/v), 10% (0.2% w/v), and 2.8% (0.4% w/v). Similar results are also illustrated in the eluate.

Figure 7:
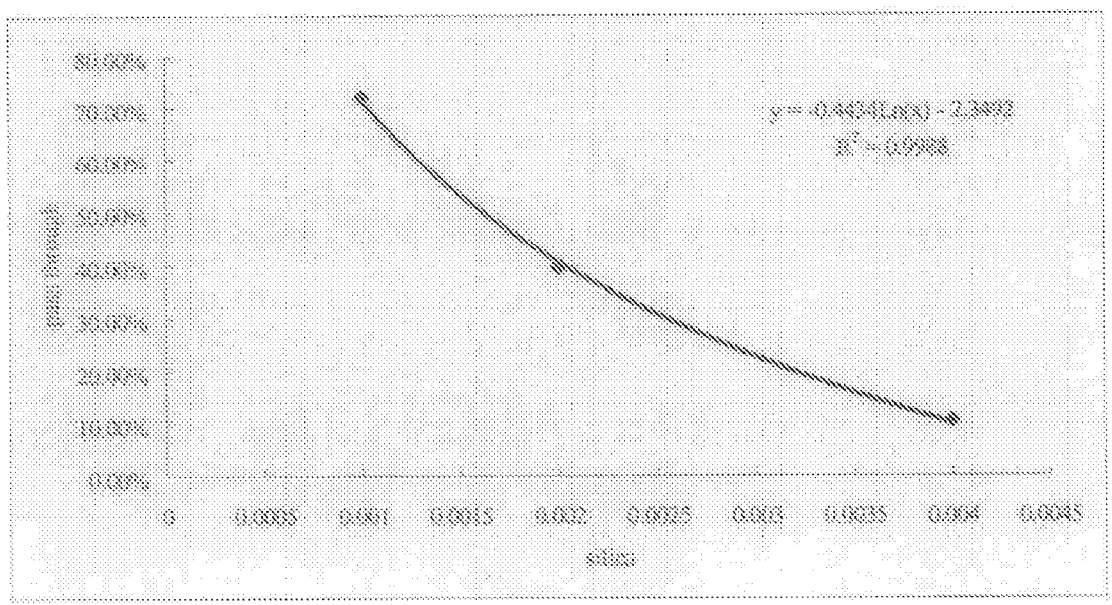
FIG. 7 illustrates the curve of the adsorption ability related to the surface area of the adsorbent.

The content of antibodies in the egg yolk extraction is about 26.3%. The adsorption ability is estimated by comparing the amounts of the antibodies in the egg yolk extraction and flow-through solution. Taking the result of 0.1% (w/v) fumed silica as an example, the adsorbed antibodies were about 27% which is adsorbed by the fumed silica with a total surface area of 0.2 $m^2$. After calculation, the curve of the adsorption ability related to the surface area was obtained and shown in FIG. 7 and Table 3. It shows that the surface area is preferably between 0.05 to 8 $m^2/g$; and more preferably between 0.1 to 2 $m^2/g$.

TABLE 3

| antibody adsorption % | silica, fumed used % (w/v) | total surface area ($m^2/g$) |
|---|---|---|
| 5% | 0.06% | 0.12 |
| 10% | 0.07% | 0.14 |
| 20% | 0.09% | 0.18 |
| 50% | 0.16% | 0.32 |
| 90% | 0.42% | 0.84 |
| 95% | 0.53% | 1.06 |
| 99% | 0.79% | 1.58 |

Figure 8A:
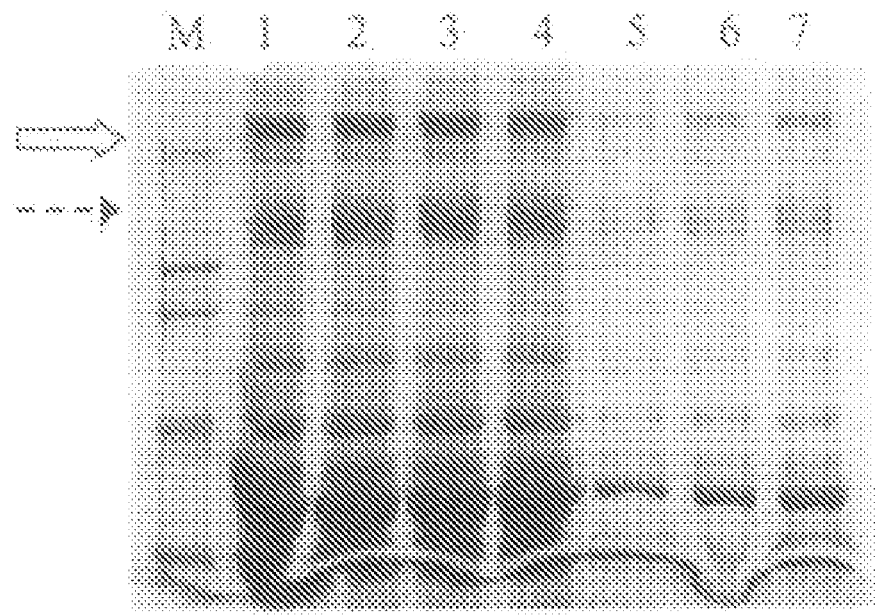
FIG. 8a illustrates a SDS-PAGE analysis comparing the antibody adsorption abilities of the Celite® diatomite; M: marker; lane 1: egg yolk extration: lane 2: flow-through solution of 2% (w/v); lane 3: flow-through solution of 4% (w/v) lane 4: flow-through solution of 8% (w/v); lane 5: eluate of 2% (w/v); lane 6: eluate of 4% (w/v); lane 7: eluate of 8%; the hollow arrow indicated the position of IgY and the arrow with dotted line indicated the position of IgY(Δ Fc)
Figure 8B:
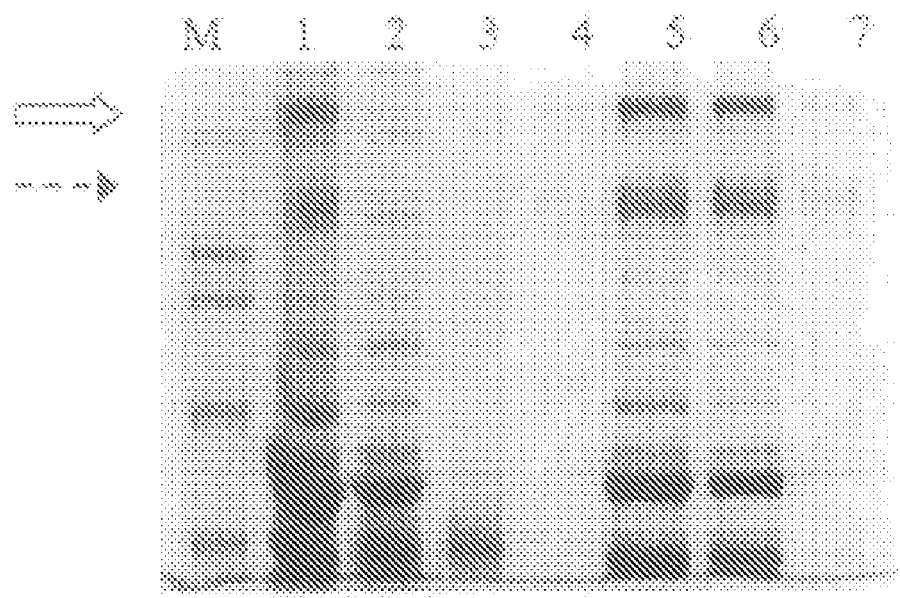
FIG. 8b illustrates a SDS-PAGE analysis comparing the antibody adsorption abilities of the Celite® diatomite hyflosupercel; M: marker; lane 1: egg yolk extration: lane 2: flow-through solution of 2% (w/v); lane 3: flow-through solution of 4% (w/v) lane 4: flow-through solution of 8% (w/v); lane 5: eluate of 2% (w/v); lane 6: eluate of 4% (w/v); lane 7: eluate of 8%; the hollow arrow indicated the position of IgY and the arrow with dotted line indicated the position of IgY(Δ Fc).

The result of Celite® diatomite is shown in FIG. 8a and that of Celite® diatomite hyflosupercel is shown in FIG. 8b. The particle size of Celite® diatomite hyflosupercel is smaller than that of Celite® diatomite. As a result, the surface area of Celite® diatomite hyflosupercel is much larger than that of Celite® diatomite. The results of FIGS. 8a and b showed that the adsorbability of Celite® diatomite hyflosupercel is better than that of Celite® diatomite. What was shown on Table 4 means the particle size of adsorbents and the correspondent possible surface area ($m^2/g$). The calculation equation is: surface area ($m^2/g$)=3/(D×r). According to the equation, even though the surface area of Celite® Diatomite is only 0.0271 $m^2/g$ when added in with the concentration of 2% (W/V), it can demonstrate the adsorbance ability with the total surface area of 0.000542 $m^2$. (Ref. FIG. 8a Lane 5, Elute of 2% Celite® shows significant antibody signal.) Therefore, we can assume that the adsorbent has the adsorbance ability when its surface area is more than 0.0005 $m^2$.

TABLE 4

| Adsorbent | Particle size | Surface area ($m^2/g$) |
|---|---|---|
| Silica, fumed | 7~14 nm | 195~390 |
| Celite diatomite | 48 μm | 0.0271 |
| Kaolin | 0.1~4 μm | 0.2884~11.5384 |
| Sigmacell, type 101 | ≧20 μm | ≦0.25 |
| Silicon dioxide | 1~5 μm | 0.2308~1.1538 |
| Silica gel, type G | 10~40 μm | 0.0357~0.1429 |
| Silica gel, type H | 10~40 μm | 0.0357~0.1429 |
| Celite, hyflosupercel | 27 μm | 0.0483 |

All patents and literature references cited in the present specification are hereby incorporated by reference in their entirety. In case of conflict, the present description, including definitions, will prevail.

While embodiments of the present invention have been illustrated and described, various modifications and improvements can be made by persons skilled in the art. The embodiments of the present invention are therefore described in an illustrative but not restrictive sense. It is intended that the present invention is not limited to the particular forms as illustrated, and that all the modifications not departing from the spirit and scope of the present invention are within the scope as defined in the appended claims.

What is claimed is:

1. A process for selectively isolating IgY antibodies from egg yolk of an anseriform bird, comprising:
   (a) adsorbing IgY antibodies in a water-miscible fraction obtained from the egg yolk of an anseriform bird with a porous water insoluble non-charged adsorbent selected from the group consisting of silicate, silicon compounds, carbonate, sulfate, phosphate, carbon, cellulose, synthetic fiber, ceramics, and metal oxide, and wherein the porous water insoluble non-charged adsorbent is at an amount effective for separating the IgY antibodies from the water-miscible fraction; and
   (b) flowing the porous water insoluble non-charged adsorbent with a buffer to obtain an aqueous fraction containing the IgY antibodies, wherein the IgY antibodies comprise antibodies with Fc regions and antibodies that lack Fc regions.

2. The process of claim 1, wherein the porous water insoluble non-charged adsorbent has a specific surface area ranging from about 0.0005 $m^2/g$ to about 8 $m^2/g$.

3. The process of claim 2, wherein the porous water insoluble non-charged adsorbent has a specific surface area ranging from about 0.1 $m^2/g$ to about 2 $m^2/g$.

4. The process of claim 1, wherein the porous water insoluble non-charged adsorbent is a silicate selected from the group consisting of synthetic or natural clays, kaolin, talc, and calcium silicate.

5. The process of claim 1, wherein the porous water insoluble non-charged adsorbent is a silicon compound selected from the group consisting of fumed silica, amorphous silica, silica dioxide, silica gel, silicates, and Fuller's earth.

6. The process of claim 5, wherein the porous water insoluble non-charged adsorbent is fumed silica.

7. The process of claim 1, wherein the porous water insoluble non-charged adsorbent comprises calcium carbonate or barium carbonate.

8. The process of claim 1, wherein the porous water insoluble non-charged adsorbent comprises calcium sulfate.

9. The process of claim 1, wherein the porous water insoluble non-charged adsorbent comprises calcium phosphate.

10. The process of claim 1, wherein the porous water insoluble non-charged adsorbent comprises activated carbon or carbon fiber.

11. The process of claim 1, wherein the porous water insoluble non-charged adsorbent is cellulose powder.

12. The process of claim 1, wherein the porous water insoluble non-charged adsorbent comprises aluminum oxide or titanium oxide.

13. The process of claim 1, wherein the anseriform bird is a duck or a goose.

14. The process of claim 1, wherein the buffer for flowing the porous water insoluble non-charged adsorbent in step (b) comprises a chaotropic salt.

15. The process of claim 14, wherein the chaotropic salt comprises about 3 M to about 6 M guanidine-HCl or about 0.1 M to about 3 M sodium thiocyanate.

16. The process of claim 1, further comprising a purification step by an immuno-affinity chromatography at a pH value ranging from about 4 to about 7 under an ionic strength of lower than about 50 mM.

17. The process of claim 16, wherein the pH value is between about 5 to about 6.

18. The process of claim 17, wherein the pH value is between about 5.6 to about 5.8.

19. The process of claim 1, wherein the aqueous fraction containing the IgY antibodies in step (b) is a flow-through solution which has flowed through the porous water insoluble non-charged adsorbent.

20. The process of claim 1, wherein the aqueous fraction containing the IgY antibodies in step (b) is an eluate eluted from the porous water insoluble noncharged adsorbent.

21. The process of claim 1, further comprising:
(c) salting out the aqueous fraction containing IgY antibodies in step (b) with $(NH_4)_2SO_4$ of a first concentration ranging from about 15% (w/v) to about 24% (w/v); and
(d) salting out the aqueous fraction containing IgY antibodies treated in step (c) with $(NH_4)_2SO_4$ of a second concentration ranging from about 25% (w/v) to about 40% (w/v) based on the volume of the aqueous fraction treated in step (c).

* * * * *

UNITED STATES PATENT AND TRADEMARK OFFICE
CERTIFICATE OF CORRECTION

| | | |
|---|---|---|
| PATENT NO. | : 8,173,783 B2 | Page 1 of 1 |
| APPLICATION NO. | : 11/409515 | |
| DATED | : May 8, 2012 | |
| INVENTOR(S) | : Victor Chiou | |

It is certified that error appears in the above-identified patent and that said Letters Patent is hereby corrected as shown below:

On the Cover Page, Column 2 (Other Publications), line 39, delete "latyrhynchos:" and insert -- platyrhynchos: --

On the Cover Page, Column 2 (Abstract), line 4, delete "absorbent" and insert -- adsorbent --

In Column 18, line 3, in claim 20, delete "noncharged" and insert -- non-charged --

Signed and Sealed this
Thirty-first Day of July, 2012

David J. Kappos
*Director of the United States Patent and Trademark Office*